US009265439B2

(12) United States Patent
Silber (10) Patent No.: US 9,265,439 B2
(45) Date of Patent: Feb. 23, 2016

(54) METHOD OF ASSESSING CENTRAL ARTERIAL STIFFNESS USING MRI, METHOD OF ASSESSING VASCULAR FUNCTION INCLUDING ARTERIAL STIFFNESS, APPLICATIONS PROGRAM AND MEDIA EMBODYING SAME

(75) Inventor: Harry A. Silber, Owings Mills, MD (US)

(73) Assignee: The Johns Hopkins University, Baltimore, MD (US)

( * ) Notice: Subject to any disclaimer, the term of this patent is extended or adjusted under 35 U.S.C. 154(b) by 678 days.

(21) Appl. No.: 12/223,007

(22) PCT Filed: Jan. 19, 2007

(86) PCT No.: PCT/US2007/001616
§ 371 (c)(1),
(2), (4) Date: Feb. 2, 2012

(87) PCT Pub. No.: WO2007/084747
PCT Pub. Date: Jul. 26, 2007

(65) Prior Publication Data
US 2012/0123240 A1      May 17, 2012

Related U.S. Application Data

(60) Provisional application No. 60/760,186, filed on Jan. 19, 2006.

(51) Int. Cl.
*A61B 5/05* (2006.01)
*A61B 5/055* (2006.01)
*A61B 5/02* (2006.01)
*G01R 33/563* (2006.01)
*G01R 33/567* (2006.01)

(52) U.S. Cl.
CPC ............. *A61B 5/055* (2013.01); *A61B 5/02007* (2013.01); *G01R 33/5635* (2013.01); *G01R 33/56308* (2013.01); *G01R 33/5673* (2013.01); *G01R 33/56316* (2013.01)

(58) Field of Classification Search
USPC .......................................... 600/407, 409, 410
See application file for complete search history.

(56) References Cited

U.S. PATENT DOCUMENTS

| 6,141,578 | A  | * | 10/2000 | Hardy ........................... 600/410 |
| 6,265,875 | B1 |   | 7/2001  | Saranathan et al. |
| 6,288,541 | B1 |   | 9/2001  | Dumoulin |
| 6,537,226 | B1 | * | 3/2003  | Marcoyannopoulou-Fojas ............................ 600/500 |
| 6,654,628 | B1 | * | 11/2003 | Silber et al. ................... 600/410 |
| 2003/0040675 | A1 |   | 2/2003  | Sharrock |
| 2004/0088123 | A1 | * | 5/2004  | Ji .................................... 702/45 |

OTHER PUBLICATIONS

Pannier et al (methods and devices for measuring arterial compliance in humans, 2002).*

* cited by examiner

*Primary Examiner* — Joel F Brutus
(74) *Attorney, Agent, or Firm* — Mintz Levin Cohn Ferris Glovsky and Popeo, P.C.; Peter F. Corless; Richard B. Emmons (57) ABSTRACT

Featured are methods for non-invasive assessment of a vascular physiological parameter including but not limited to central arterial stiffness, vascular reactivity and/or local arterial stiffness. The methods of the invention use any one of a number of magnetic resonance imaging techniques known in the art to acquire image data so as to arrive at these vascular physiological parameters. Also such methods include locating the detector or imaging coil proximal to a single artery and external to the body/specimen. According to one aspect, the methodology determines the central arterial stiffness from image data acquired at the single arterial location. In another aspect, image data is acquired so that one or more of central arterial stiffness, vascular reactivity and/or local arterial stiffness can be determined from the acquired image data alone or in combination with other acquired data/information. The disclosed methods of the invention allow for reproducible, non-invasive diagnosis of early stage indicators of atherosclerosis.

17 Claims, 6 Drawing Sheets

METHOD OF ASSESSING CENTRAL ARTERIAL STIFFNESS USING MRI, METHOD OF ASSESSING VASCULAR FUNCTION INCLUDING ARTERIAL STIFFNESS, APPLICATIONS PROGRAM AND MEDIA EMBODYING SAME

This application claims the benefit of U.S. Provisional Application Ser. No. 60/760,186 filed Jan. 19, 2006, and is related to PCT/US2006/02261 filed Jan. 19, 2006, the teaching of all of which are incorporated herein by reference.

STATEMENT REGARDING FEDERALLY-SPONSORED RESEARCH

The present invention was made with government support under K23-HL-004477 from the National Heart, Lung and Blood Institute. The U.S. Government may have certain rights to the present invention.

FIELD OF INVENTION

The present invention relates to methods of assessing arterial stiffness, more particularly, methods of assessing arterial stiffness from a single peripheral arterial location using a non-invasive technique such as magnetic resonance imaging and even more particularly to methods of assessing arterial stiffness and vascular reactivity (e.g., endothelial function).

BACKGROUND OF THE INVENTION

Atherosclerotic cardiovascular disease is the leading cause of death in developed nations. Traditional risk factors predict atherosclerotic disease in populations but lack specificity in predicting atherosclerosis severity in individuals.

Since modifiable risk factors account for most myocardial infarctions worldwide, early and accurate identification of high-risk individuals would allow better targeting of aggressive preventive strategies. Yusuf S, Hawken S, Ounpuu S, et al. Effect of potentially modifiable risk factors associated with myocardial infarction in 52 countries (the INTERHEART study): case-control study. Lancet 2004; 364:937-52. The incidence of coronary heart disease can be predicted in populations based on traditional risk factors [Wilson P W, D'Agostino R B, Levy D, Belanger A M, Silbershatz H, Kannel W B. Prediction of coronary heart disease using risk factor categories. Circulation 1998; 97:1837-47], but these factors lack specificity in predicting severity of atherosclerosis and likelihood of cardiovascular events in individuals [Greenland P, LaBree L, Azen S P, Doherty T M, Detrano R C. Coronary artery calcium score combined with Framingham score for risk prediction in asymptomatic individuals. Jama 2004; 291:210-5; Desai M Y, Nasir K, Braunstein J B, et al. Underlying risk factors incrementally add to the standard risk estimate in detecting subclinical atherosclerosis in low- and intermediate-risk middle-aged asymptomatic individuals. Am Heart J 2004; 148:871-7]. Consequently, other noninvasive methods are needed beyond traditional risk factors for early and accurate identification of individuals at high risk for atherosclerosis.

As is known to those skilled in the art, abnormalities of two arterial properties—endothelial function and central arterial stiffness—are associated with increased risk of atherosclerosis and cardiovascular events [Schroeder S, Enderle M D, Ossen R, et al. Noninvasive determination of endothelium-mediated vasodilation as a screening test for coronary artery disease: pilot study to assess the predictive value in comparison with angina pectoris, exercise electrocardiography, and myocardial perfusion imaging. Am Heart J 1999; 138:731-9; Neunteufl T, Katzenschlager R, Hassan A, et al. Systemic endothelial dysfunction is related to the extent and severity of coronary artery disease. Atherosclerosis 1997; 129:111-8; Teragawa H, Kato M, Kurokawa J, Yamagata T, Matsuura H, Chayama K. Usefulness of flow-mediated dilation of the brachial artery and/or the intima-media thickness of the carotid artery in predicting coronary narrowing in patients suspected of having coronary artery disease. Am J Cardiol 2001; 88:1147-51; Oliver J J, Webb D J. Noninvasive assessment of arterial stiffness and risk of atherosclerotic events. Arterioscler Thromb Vasc Biol 2003; 23:554-66; Sutton-Tyrrell K, Najjar S S, Boudreau R M, et al. Elevated aortic pulse wave velocity, a marker of arterial stiffness, predicts cardiovascular events in well-functioning older adults. Circulation 2005; 111:3384-90].

Furthermore, endothelial dysfunction and increased central arterial stiffness precede atherosclerosis by years or even decades [Celermajer D S, Sorensen K E, Gooch V M, et al. Non-invasive detection of endothelial dysfunction in children and adults at risk of atherosclerosis. Lancet 1992; 340:1111-5; Iannuzzi A, Licenziati M R, Acampora C, et al. Preclinical changes in the mechanical properties of abdominal aorta in obese children. Metabolism 2004; 53:1243-6; Wildman R P, Mackey R H, Bostom A, Thompson T, Sutton-Tyrrell K. Measures of obesity are associated with vascular stiffness in young and older adults. Hypertension 2003; 42:468-73].

Hence, there is much interest in developing noninvasive techniques for assessing endothelial function and/or central arterial stiffness in order to enhance cardiovascular risk stratification [Taylor A J, Merz C N, Udelson J E. 34th Bethesda Conference: Executive summary—can atherosclerosis imaging techniques improve the detection of patients at risk for ischemic heart disease? J Am Coll Cardiol 2003; 41:1860-2; Corretti M C, Plotnick G D, Vogel R A. Technical aspects of evaluating brachial artery vasodilatation using high-frequency ultrasound. Am J Physiol 1995; 268:H1397-404; Kuvin J T, Patel A R, Sliney K A, et al. Peripheral vascular endothelial function testing as a noninvasive indicator of coronary artery disease. J Am Coll Cardiol 2001; 38:1843-9; Moens A L, Goovaerts I, Claeys M J, Vrints C J. Flow-mediated vasodilation: a diagnostic instrument, or an experimental tool? Chest 2005; 127:2254-63]. Thus, evaluating either or both of these arterial properties may enable early and accurate identification of high-risk individuals.

A standard approach to assessing central arterial stiffness is to measure central pulse wave velocity—pulse waves travel faster in stiffer arteries. There are two particular methods of assessing central pulse wave velocity that typically measure transit time between two different aortic sites [Mohiaddin R H, Firmin D N, Longmore D B. Age-related changes of human aortic flow wave velocity measured noninvasively by magnetic resonance imaging. J Appl Physiol 1993; 74:492-7; Rogers W J, Hu Y L, Coast D, et al. Age-associated changes in regional aortic pulse wave velocity. J Am Coll Cardiol 2001; 38:1123-9] or two peripheral arterial sites [Davies J I, Struthers A D. Pulse wave analysis and pulse wave velocity: a critical review of their strengths and weaknesses. J Hypertens 2003; 21:463-72].

When assessing central pulse wave velocity by measuring transit time between two different aortic sites, the aorta—the major artery in the chest—is imaged using MRI and the arrival time of the pulse wave at two or more aortic locations is determined. The distance between each of two points is typically determined using the acquired image and the pulse wave velocity is determined using the difference between the arrival times at two locations and the distance between these two points (i.e., $V_{pw}$=distance/time, where the distance and time is that between the two locations). This particular methodology can involve breath-holding and can involve time-consuming scanning and data analysis.

In the other methodology where two peripheral sites are used, the difference in pulse-wave arrival times at two different peripheral arterial locations, such as the radial and femoral arteries is determined. Also, the distance between these two peripheral arterial locations is determined. In the common technique often called applanation tonometry, two transducer or sensors are located external to the body and in proximity to the peripheral arterial locations. The transducers can be used to generate a time history of pressure changes and thereby sense the arrival of a pulse wave. The distance between these two peripheral arterial locations is typically determined by extending a tape measurer between the locations of the two sensors.

As indicated above, vascular physiology can be assessed, in part, through measurements of endothelial function. Changes in the diameter of an artery in response to a stimulus such as change in blood flow velocity through the artery (arterial wall shear stress, WSS) are indicative of endothelial function, known as flow mediated dilation (FMD). Endothelial function can be measured by inflating a blood pressure cuff around a subject's arm and monitoring velocity of blood flowing through a brachial artery while measuring the artery's diameter before, during and after the inflation of the cuff.

Vascular endothelium, the inner lining of blood vessels, is crucially important to maintaining vascular health. Endothelial cells regulate thrombosis, inflammation, vasomotion, and cell proliferation through the synthesis and release of substances including nitric oxide and endothelin-1. Cardiovascular risk factors are associated with endothelial dysfunction, and agents that reduce cardiovascular risk also improve endothelial function. Hence, endothelial dysfunction is considered to be an important common pathway by which risk factors promote atherosclerosis. Furthermore, endothelial dysfunction is associated with coronary events. Consequently, there is much interest in assessing endothelial function non-invasively.

It thus would be desirable to provide new non-invasive methods for assessing central arterial stiffness using a non-invasive imaging technique such as Magnetic Resonance Imaging (MRI) as well as applications programs embodying such methods. It would be particularly desirable to provide such methods that would assess central arterial stiffness by use of image data acquired at a single peripheral arterial location such as for example, the femoral artery. It also would be desirable to provide new non-invasive methods whereby one acquires image data to assess one or more vascular properties, such as central arterial stiffness, local arterial stiffness and/or vasculature reactivity using a non-invasive technique (e.g., MRI) at a single peripheral arterial location such as for example, the femoral artery, as well as applications programs embodying such methods. Such a method would be particularly adaptable so that the image data for these one or more vascular properties is obtained without having to reposition or relocate the detector or imaging coil used to acquire the image data.

The references referred to herein and discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention features methods for non-invasive assessment of central arterial stiffness of a mammal, such as a human being, using a non-invasive technique such as Magnetic Resonance Imaging (MRI). In more particular aspects, such assessment is made by imaging a single arterial location, more specifically a single peripheral arterial location, so as to determine an arrival time of a pulse wave at that location. In more particular embodiments, such methods include using phase contrast magnetic resonance imaging to obtain the image data of the vasculature being evaluated. In yet more particular embodiments, the single peripheral arterial location is selected so that the pulse wave being detected has traversed the central arteries and in yet further embodiments the image data is acquired from the femoral artery.

Further such methods, include using the acquired image data to determine a parameter that is relatable to central arterial stiffness and which can be used to determine a change in such stiffness. For example, the parameter can be the arrival time of the pulse wave (pulse wave arrival time and/or pulse wave velocity). Also featured are applications programs for execution on a microprocessor or computing device to process the image data and so as to yield such pulse wave arrival times and/or pulse wave velocity. Such applications programs and methods further embody one or more algorithms to determine or detect passage of a pulse wave at the location being imaged.

According to yet another aspect, the methodology of the present invention is adaptable to determine any of a number of vascular physiological parameters at the single arterial location. In more particular embodiments, such vascular physiological parameters include central arterial stiffness, vascular reactivity and/or local arterial stiffness. In yet more particular embodiments, the image data acquired for determining the above, can be acquired while the detection device or imaging coil/antenna is located at the single peripheral location. In this way, image data is acquired for each of the one or more vascular physiological parameters without the patient or specimen being scanned to be withdrawn from the bore of the main magnet or to be re-positioned within the bore of the main magnet or without re-positioning of the detector or imaging coil/antenna.

As indicated herein, according to an embodiment of the present invention, there is featured a methodology for assessing central arterial stiffness using image data acquired using an MRI technique to determine a central arterial stiffness related parameter. Such a method includes:

(a) locating an MRI detection device external to a body or specimen to be imaged and proximal to a single artery; more particularly, a single peripheral artery;

(b) acquiring image data using an MRI imaging process, the image data being acquired in a time sequence, (c) determining from the acquired image data passage of one or more fluid pulses in the single artery/single peripheral artery (i.e., at the location being imaged); and (d) determining a central arterial stiffness related parameter using information relating to the determined one or more fluid pulses.

In yet more particular exemplary embodiments, the central arterial stiffness related parameter is pulse wave velocity and the methodology includes determining a pulse wave arrival time for each of the one or more pulses; determining a distance from a specified feature of the body or specimen to the location of the detector/imaging coil; and calculating a pulse wave velocity based on the determined distance and an elapsed time from a cardiac event to the determined pulse wave arrival time for each of the one or more pulse waves.

Such a method for MRI assessment of central arterial stiffness at a single peripheral location, such as the proximal femoral artery, is easily accessible by MRI, does not require breath-holding, is automated and user-independent. Such methods also should save time as compared to that for two-peripheral-location methods, and it also would same time if one measures vascular reactivity during the same measurement session. Thus, it not only has advantages over other MRI methods, but also has advantages over non-MRI techniques, such as applanation tonometry or ultrasound.

As indicated herein, according to an embodiment of the present invention, there also is featured a methodology for assessing one of central arterial stiffness and vascular reactivity, where assessing vascular reactivity includes measuring shear rate, vasculature dimension and/or flow of fluid in the vasculature at a time when vasculature is being occluded. In more particular embodiments, the methods for assessing central arterial stiffness are combined with MRI methods for analyzing vascular endothelial function at the same single peripheral location. This allows a comprehensive, user-independent, automated assessment of vascular function.

In exemplary embodiments, such a method for assessing vascular reactivity more particularly includes:

(a) using a magnetic resonance imaging scanner to obtain images;

(b) locating an artery using coronal scout images;

(c) positioning the subject or patient, such that the artery is parallel to a magnet bore of the magnetic resonance imaging scanner and cross sectional images can be thus obtained;

(d) constricting the artery for a time period, whereby the artery is fully occluded;

(e) acquiring images of the artery prior to occlusion (at baseline), during one or more times during occlusion and after release of occlusion;

(f) using the acquired image data and measuring the shear rate and/or radius of the artery at baseline, for each of the one or more times during occlusion and after occlusion release; and (g) determining from the measured values if the values are outside the range of normal individuals, whereby a outside the range is indicative of abnormal vascular endothelial function.

Such methods are particularly advantageous as the methodology provides a mechanism by which people at risk for atherosclerosis development, even years before atherosclerosis develops in them, can be identified non-invasively. Such methods are beyond just screening patients at risk for atherosclerosis, the present invention provides the type of analysis and data for the development and use of anti-atherosclerotic primary preventive or secondary preventive therapy. Also, and as indicated herein, the applications program(s) or the software package of an MRI scanner for new MRI scanners can be adapted, or the program could be sold to end-users as a software upgrade for existing MRI scanners either currently with or without cardiovascular software.

As indicated herein the present invention also features an application or software program for execution on a computer, computing device or microprocessor as is known to those skilled in the art. Such software or applications program includes code segments, instruction and criteria to acquire the image data, to process the image data so as to determine central arterial stiffness and/or measure the shear rate, the radius of the artery and/or the flow through the artery as embodied in and described herein for any of the methodologies of the present invention. Also featured is a computer readable medium on which is stored such an applications program or software.

In further embodiments, there is featured a data processing system including a computer, computing device or microprocessor as is known to those skilled in the art and an applications program or software as herein described, which is loaded onto the computer, computing device or microprocessor for execution therein.

Other aspects and embodiments of the invention are discussed below.

DEFINITIONS

The instant invention is most clearly understood with reference to the following definitions:

A computer readable medium shall be understood to mean any article of manufacture that contains data that can be read by a computer or a carrier wave signal carrying data that can be read by a computer. Such computer readable media includes but is not limited to magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; paper media, such as punched cards and paper tape; or on carrier wave signal received through a network, wireless network or modem, including radio-frequency signals and infrared signals.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

The present invention features various methods that can assess any of a number of vascular physiological parameters including central arterial stiffness, local arterial stiffness and endothelial function using any of a number of MRI techniques and more particularly using phase contrast magnetic resonance angiography. Overall, the methods of the present invention enhance the assessment of one or more vascular physiological parameters.

Phase contrast magnetic resonance angiography (PC-MRA) allows for images which can provide cross sectional area and spatially blood flow velocity readings simultaneously; thus, it readily allows for the measurement of vascular wall shear rate, simultaneous measuring the radius of the vasculature when dilated or contracted, detecting arrival of a pulse wave and the like. A fixed cross section can be imaged repeatedly, thus reducing operator dependence.

As discussed herein, the methods of the present invention allow for assessing central arterial stiffness using MRI (e.g., PCMRA). In general and according to one aspect of the present invention, such methods comprise or consist of the following:

a person lies in scanner with a receiver coil located proximal to an artery, more particularly a peripheral artery;

magnetic resonance images are obtained of the arterial cross section of the singe arterial location in a time sequence;

the arrival of each pulse wave is determined from the acquired image data;

a central arterial stiffness related parameter (e.g., pulse wave velocity) is determined based on the detected/determined arrival or passage of one or more of the pulse waves at the single arterial location.

As also discussed herein, the methods of the present invention allow for assessing vascular endothelial function using phase contrast magnetic resonance angiography (PCMRA). In general and according to one aspect of the present invention, such methods comprise or consist of the following:

a person lies in scanner with a receiver coil and a sphygmomanometer, or inflatable cuff (e.g., inflatable blood pressure cuff) on the limb;

phase contrast magnetic resonance images are obtained of the arterial cross section at baseline;

the cuff is inflated to a pressure above the maximum systolic pressure of the person in order to block the artery completely, for a period of about five minutes; and phase contrast magnetic resonance images are obtained of the arterial cross section at time intervals while the artery is blocked and after the occlusion is released.

Figure 1:
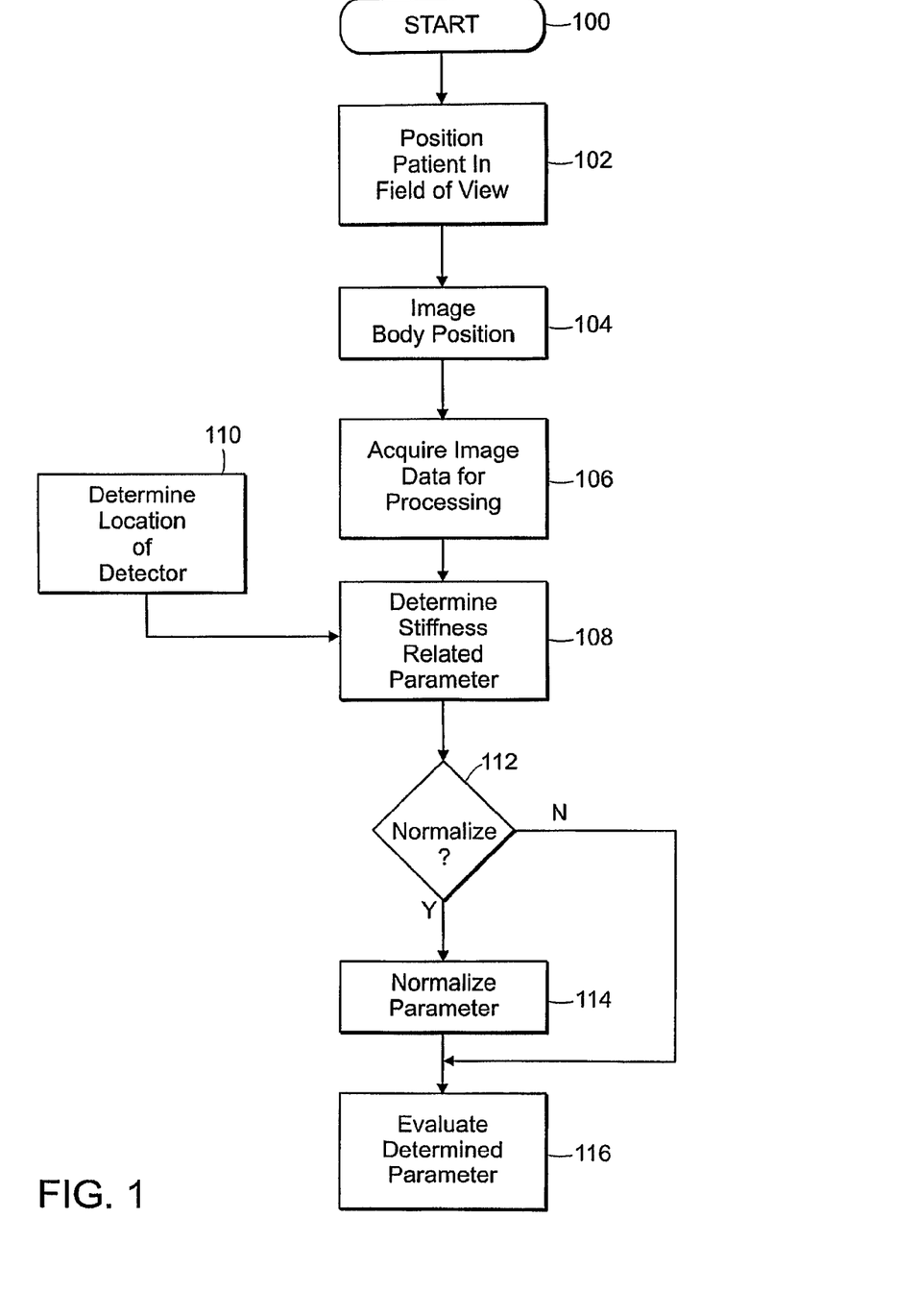
FIG. 1 is a high level flow diagram of a methodology for assessing central arterial stiffness according to one aspect of the present invention.

Referring now to FIG. 1, there is shown a high level flow diagram of a methodology for determining central arterial stiffness the present invention. It is within the scope and skill of those knowledgably in the art to adapt the below described methodology so as to be used with pixel arrays of different sizes and arrangements as well as subset arrays of different arrangements and configurations than that described below.

The methodology is started, Step 100 at the time a patient is to be imaged using an MRI technique to acquire the image data for processing in accordance with the present invention. Such starting includes preparing the MRI devices and apparatus that are to be used to carryout the imaging. In particular, such starting includes locating the detector(s), detection device(s) or imaging coil(s)/antenna(s) proximal to the artery and location of such an artery being imaged. In more particular embodiments, the artery is a peripheral artery such as for example the femoral artery. In general the peripheral artery is selected so that the pulse wave being detected and used to determine the central arterial stiffness related parameter has passed through the central arteries. MRI devices and apparatus are well known in the art.

Before acquiring the image data that is to be processed as described herein, the patient is arranged or positioned so that the region or area of interest, more specifically the vasculature cross-section to be imaged, will be located or positioned in the center of the image, Step 100. As indicated above, the coil/detector also is arranged with respect to the patient so as to be proximal to the vasculature cross-section to be imaged. It should be recognized that while it is desirous to position the cross-section of the vasculature to be imaged so it would be generally located or positioned in the center of the image, it is within those skilled in the art to adapt the below described procedure so that it can process an image where the cross-section of the vasculature to be imaged would not be located or positioned in the center in the image. Typically, and as described below in the examples, one images the object or patient before acquiring the image data to be processed so as to position the object/person for data acquisition.

After the patient or object is so positioned or, at some time following the imaging process, the clinician or technician determines the location of the detector/coil with respect to a specific anatomical feature of the patient r specimen, Step 110. More particularly, such determining includes determining the distance between the anatomical feature and the detector/coil. For example, the distance between the sternal notch and the detector/coil is determined such as by extending a measuring ruler between these two points.

After the patient or object is positioned, the clinician or technician images the body portion, Step 104 so as to acquire image data in a time sequence. After the image data is obtained, the imaged data is acquired (L e., imported into the computer) for processing, Step 106. More particularly, a pixel array of a magnitude image or the phase image (for example a 256 by 256 pixel array) is acquired for processing. It should be recognized that the pixel array can form any of a number of numerical arrays as is known to those skilled in the art.

After acquiring the image data, a central arterial stiffness related parameter is determined, Step 108. In one illustrative embodiment, the acquired image data is reconstructed so as to allow the determination of the passage or arrival of each pulse wave at the arterial location being imaged as well as an arrival time for such passage or arrival. In one embodiment, the arterial stiffness related parameter is the elapsed time between the occurrence of a cardiac function (e.g., R-wave trigger) and the arrival time of the pulse wave corresponding or relating to the arriving pulse wave, hereinafter the pulse arrival time. In more specific embodiments, the pulse arrival times are averaged or otherwise processed using an accepted mathematical technique to arrive at a representative pulse arrival time.

Figure 3:
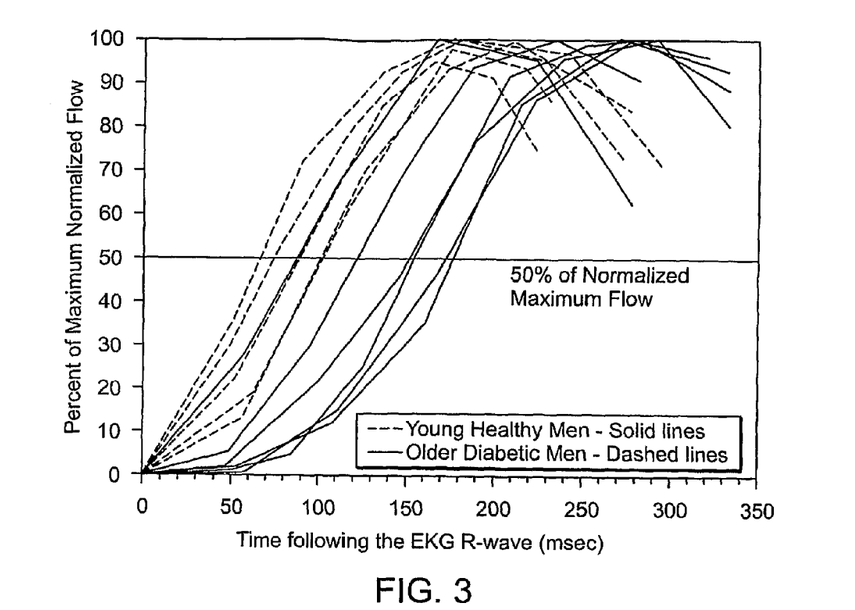
FIG. 3 a graphical view of percent of maximum normalized flow versus arrival time in the femoral arteries of young, healthy men (solid lines) versus older diabetic men (dashed-lines). The average pulse arrival time is reduced for the older diabetic men, indicating stiffer central arteries.

For example, using phase-contrast MRI, the elapsed time between the ECG trigger for the scan (ECG is typically used to trigger the scans) and the arrival of the pulse wave at the femoral artery is determined. In an illustrative exemplary embodiment, the arrival of the pulse wave is defined as when the flow in the cross-section rises to 50% of its peak value as illustrated in FIG. 3. This shall not be considered as limiting as the arrival of a pulse wave can be defined as corresponding to when the instantaneous flow rises to any of a number of values between 0 and 100%.

In another illustrative embodiment, the central arterial stiffness related parameter is the pulse wave velocity. In such a case the pulse arrival time for each pulse or a representative pulse arrival time and the determined distance from the anatomical feature and the detector/coil are used to determine the pulse wave velocity according to the following relationship, where distance is the determined or measured distance and time is the pulse arrival time as determined herein.

$$V_{pw} = \text{distance/time}$$

As indicated above, it is contemplated that one or more (e.g., a plurality or multiplicity) of pulse waves are to be detected and thus one or more pulse arrival times would be determined for each of the detected pulse waves. Thus, it is contemplated and therefore within the scope of the present invention for an average or representative pulse wave velocity to be determined using the one or more pulse wave arrival times.

As the transit length from the anatomical feature (e.g., origin of the aorta) to the proximal detector/coil (e.g., the superficial femoral artery) varies mostly with subject height, in further embodiments a determination is made whether the determined stiffness related parameter is to be normalized, Step 112. If this is the case (Yes, Step 112), then the determined parameter is normalized using any of a number of techniques or algorithms known to those skilled in the art, Step 114.

For example, in an illustrative embodiment, the pulse arrival time or the pulse transit time is normalized by multiplying by the subject's height divided by 6 ft (i.e., $T_{norm}=T_{pa} \times (H/72 \text{ in.})$, where $T_{norm}$ is the normalized time, $T_{pa}$ is the pulse arrival time, H is height of the patient).

If the determine parameter is not to be normalized (No, Step 112) or after normalizing the parameter (Step 114), the determined stiffness related parameter is evaluated to determine if the arterial stiffness is representative of age related stiffness or is indicative of an abnormal stiffness, Step 116. As is well known in the art, normal aging causes the central arteries to get stiffer. Such a determination or evaluation is made with reference to data compilations of surveys or experiments of age related stiffness and stiffness that is attributable to a vascular abnormality or a potential for future vascular abnormality.

Referring now to FIGS. 2A-D, there is shown another high level flow diagram of a methodology for assessing vascular function according to another aspect of the present of the present invention. According to this aspect of the present invention, the methodology is established so as to allow various vascular functions to be assessed while a single artery or cross-section thereof is imaged to acquire the image data necessary to assess such function.

In this regard, reference shall be made to the discussion herein regarding Steps 100 and 102 of FIG. 1 for details of Steps 200 and 202 of FIG. 2A, not otherwise described herein below. As to the methodology of the present invention, it should be recognized that the patient would be prepared so that any additional instrumentation or devices would be provided so a determination of local arterial stiffness or vascular reactivity can be made. For example, in regards to vascular reactivity, an inflatable cuff would be provided so the blood vessel could be occluded during image data acquisition and a blood pressure cuff would be provided to detect blood pressure for local arterial stiffness.

After, Steps 200 and 202, a determination is made whether to assess central arterial stiffness, Step 204. As indicated herein, in a particular exemplary embodiment, it is contemplated that the assessment method of the present invention includes assessing central arterial stiffness and vascular reactivity. Thus, if an assessment of central arterial stiffness is to be performed (Yes, Step 204), then the process proceeds to Step 220 of FIG. 2B. The process illustrated on FIG. 2B is similar to that shown on FIG. 1, as such reference shall be made to the discussion for steps 104-116 of FIG. 1 for Steps 220-232 except as other wise described below.

Figure 2A:
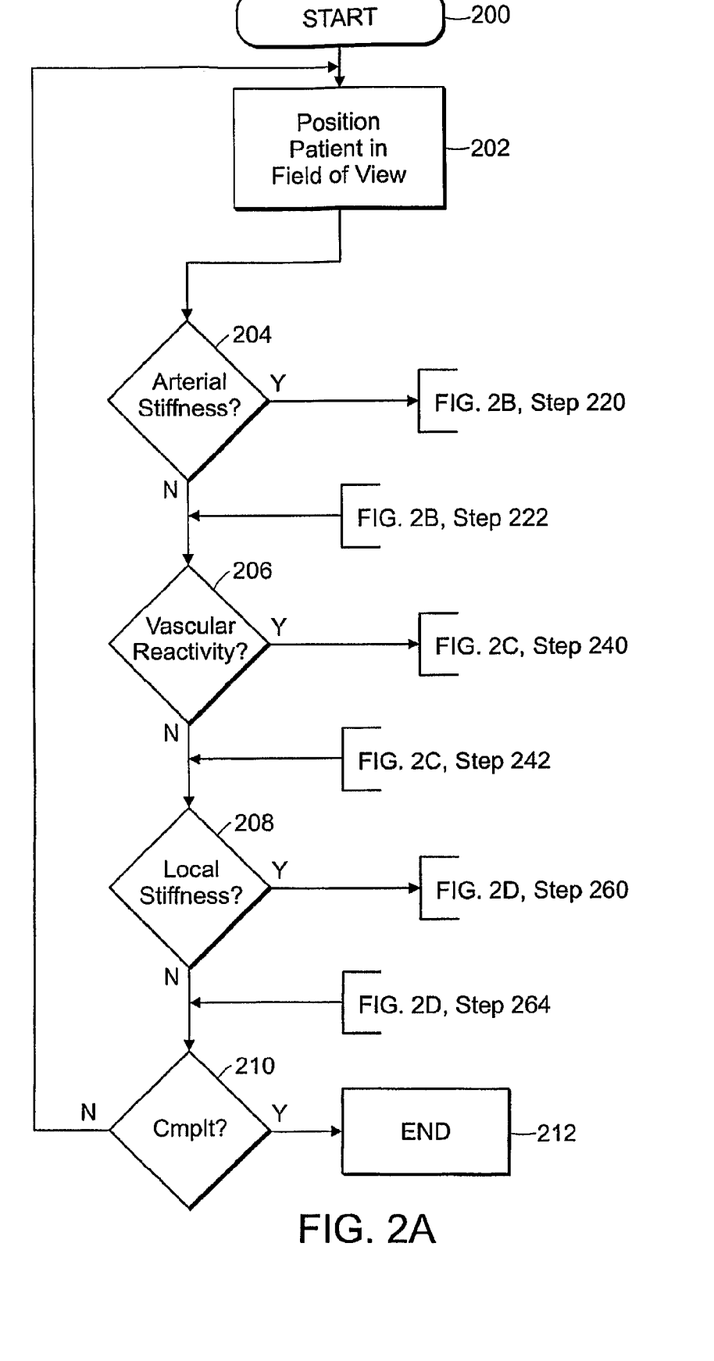
FIGS. 2A-D is another high level flow diagram of a methodology for assessing vascular function according to another aspect of the present of the present invention.

After proceeding with Steps 220 and 222, the methodology returns to continue with Step 206 of FIG. 2A. Thereafter, the process described in Steps 224-232 is conducted while image data for another vascular function is being acquired or the clinician or technician awaits the acquisition of all image data for all vascular functions to be evaluated and then conducts the process in these steps.

Figure 2B:
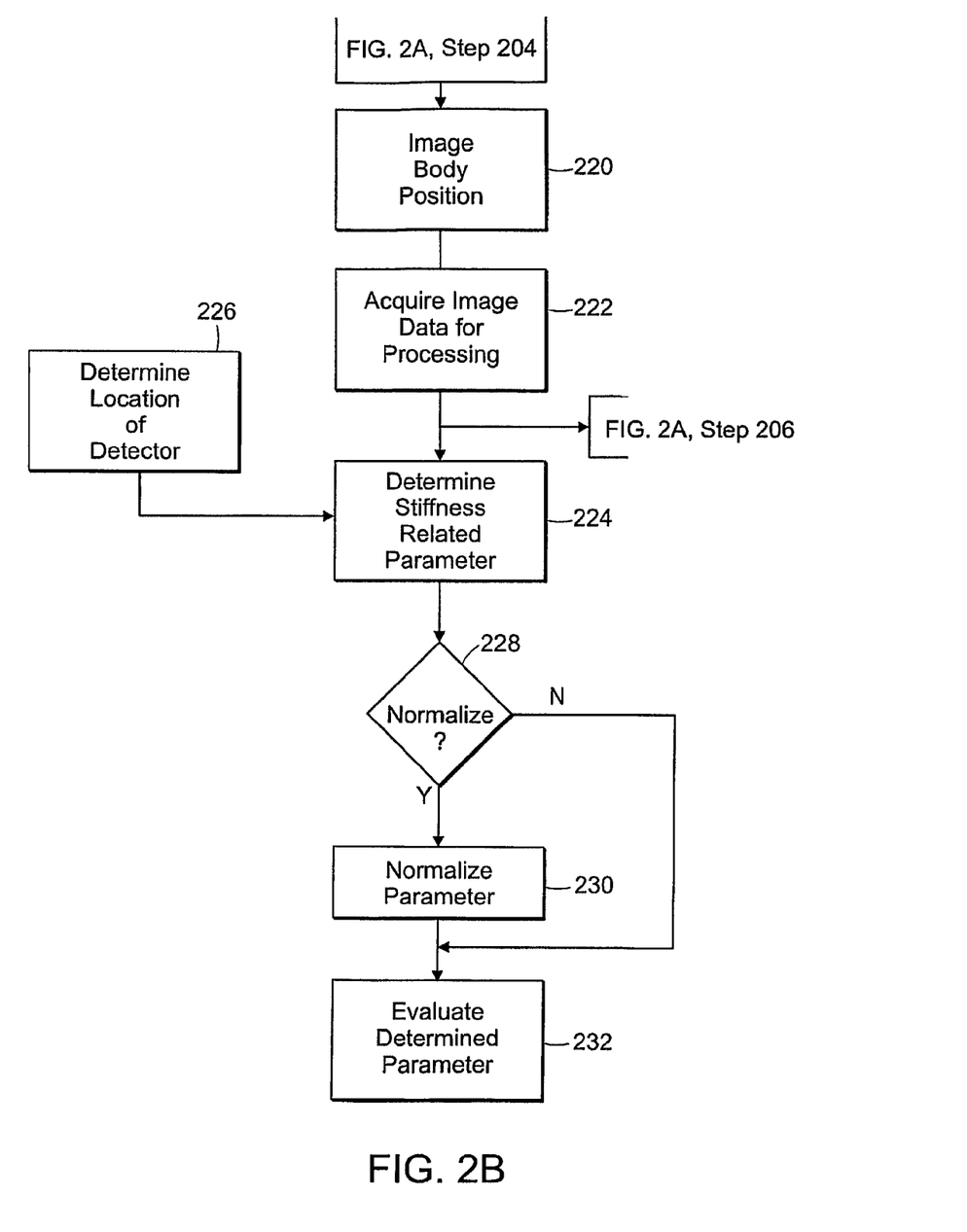

If central arterial stiffness is not be evaluated (No, Step 204) or upon return of the process to Step 206 from, Step 222 of FIG. 2B, the process continues with a determination if vascular reactivity should be assessed, Step 206. If vascular reactivity is to be assessed (Yes, Step 206), then the process proceeds to Step 240 of FIG. 2C. In regards to Steps 240-256 and the assessment of vascular reactivity reference is made to the teachings of PCT application number PCT/US2006/02261 filed Jan. 19, 2006, the teachings of which are incorporated herein by reference for teachings not described herein as well as analysis and evaluation of examples relating to that methodology.

Figure 2C:
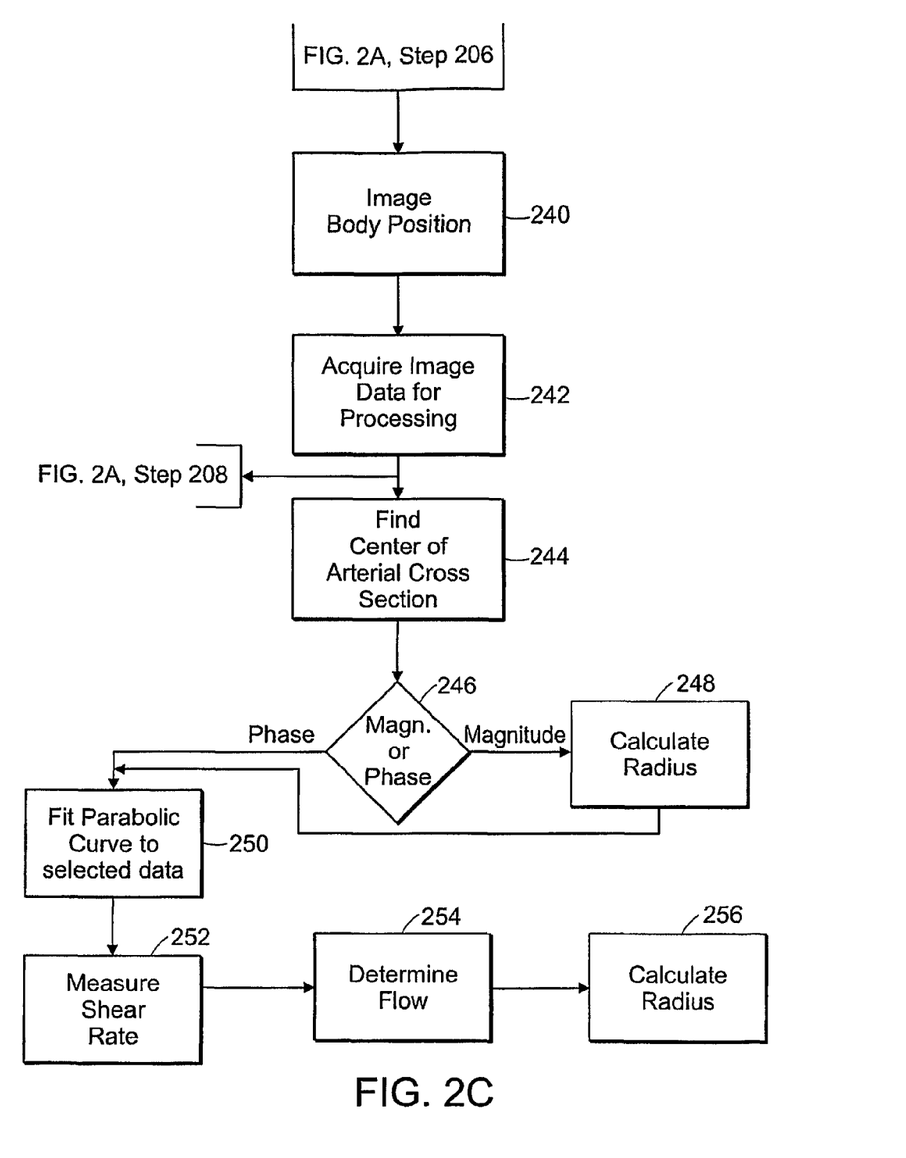

Referring to FIG. 2C, there is shown a flow diagram of a user-independent algorithm that is usable to determine radius of an arterial cross section from the magnitude image or phase image of a phase-contrast MRI scan and also to determine the shear rate and flow velocity of an arterial cross-section from the phase image of a phase-contrast MRI scan. It is within the scope and skill of those knowledgably in the art to adapt the below described algorithm so as to be used with pixel arrays of different sizes and arrangements as well as subset arrays of different arrangements and configurations than that described below.

After the patient or object is positioned, the clinician or technician images the body portion, Step 240. After the image data is obtained, the imaged data is acquired (i.e., imported into the computer) for processing, Step 242. More particularly, a pixel array of a magnitude image or the phase image (for example a 256 by 256 pixel array) is acquired for processing. It should be recognized that the pixel array can form any of a number of numerical arrays as is known to those skilled in the art.

After acquiring the pixel array, and using the magnitude or phase image the center of the arterial cross-section is determined, Step 252. In a particular illustrative embodiment the center of the arterial cross section is determined using the following steps.

1. Take a subset (e.g., a 40×40 subset) from the center of the pixel array.
2. Consider a box of pixels (e.g., a 5×5 box of pixels) inside the subset array and move that box around the array.
3. Locate the center of the box array position with the highest average intensity.
4. Use the value of the average intensity of that box as the maximum intensity inside the arterial cross-section.
5. Average the pixels in the areas surrounding the largest possible arterial cross-section and use that value as the background or zero intensity.
6. Calculate intensity range (i.e., intensity range=#6 minus #7).
7. Choose a plateau level, from 10% to 150% of the intensity range
8. Make a new subset array (e.g., a 40×40 array) called "Top" and for each pixel in the original subset array, if the pixel intensity is greater than the plateau value, set the corresponding pixel in the Top array equal to the plateau value. Otherwise, set the pixel equal to that of the original subset array. This has the effect of chopping off the top of the magnitude or phase profile.
9. Make a new subset array (e.g., a 40×40 array) called "Plateau" and for each pixel, if the corresponding pixel and any other pixel adjacent to it in Top are equal to the plateau value, set that pixel to 1. Otherwise, set that pixel equal to 0. Set the outer 1-pixel frame of pixels equal to 0.
10. Make a new subset array (e.g., a 40×40 array) called "Mass" and for each pixel in Mass, if the corresponding pixel in Plateau equals 1, add one to the contiguous pixels in Plateau that equal 1, up to five pixels away in any orthogonal direction. Make that sum the value of the pixel in Mass. Set the outer 5-pixel-wide frame of pixels to 0.
11. Find the maximum pixel value in the Mass array. Maximum possible value equals 21.

12. Make a new subset array (e.g., a 40×40 array) called "Peak." For each pixel, if its value in Mass equals the maximum pixel value in Mass, set the pixel equal to 1. Otherwise, set it equal to 0.
13. Find the geometric center of the Peak array.
14. Make a radial plot of the original data minus the calculated background level, using that geometric center as the center.
15. Make a smoothed average of the radial plot.
16. Calculate the dispersion of points by taking a sum of squares of the distance between each point and the smoothed average.
17. Repeat steps 7-16 for each plateau level.
18. Choose the plateau level that resulted in the lowest dispersion, i.e. the least sum of squares. Use the coordinates of the center that resulted from using the chosen plateau level.
19. Move the center one-half pixel in each orthogonal direction or in both orthogonal axes. There will then be nine possible center locations.
20. For each of the nine possible positions of the new center, calculate the dispersion of points around the smoothed average using the sum of squares method.
21. Choose the adjusted center that resulted in the least sum of squares.

Thereafter, the process proceeds based on whether the image used in determining the center of the arterial cross-section is the magnitude image or the phase image, Step 246. If the magnitude image was used to find the center (Step 246, magnitude), then the radius of the arterial cross-section is calculated or determined, Step 248. In an illustrative exemplary embodiment, the radius is calculated by calculating the distance from the adjusted center to where the intensity drops to half its maximum value. Thereafter, the process proceeds to Step 250.

If the phase image data was used to find the center (Step 246, phase) or after calculating the radius in Step 248), then the process proceeds to fit a parabolic curve to the velocity data of the phase image, Step 250. In a particular illustrative embodiment the fitting of the parabolic curve to the velocity data is obtained using the following steps.

A. Make a larger subset array (e.g., an 80×80 subset array) from the center of the original pixel array of the phase image.
B. Average the pixels in the areas surrounding the largest possible arterial cross-section and use that value as the background or zero velocity.
C. Take a 40×40 subset from the center of the 256×256 array of the phase image.
D. Using the adjusted center calculated from steps 1-23, make a radial plot of the phase data minus the background.
E. Find the maximum velocity of the phase data.
F. Find the radius where the velocity drops below a preset percentage of the maximum velocity. In particular embodiments, the preset percentage of the maximum velocity is in the range of from about 5 to 20% and in an exemplary embodiments is about 15%
G. Using that radius or first point 160 as the outer limit, identify a radial segment that is between that first point and a second point that is located a preset distance inward toward the center. In particular embodiments, the preset distance is in the range of between about 10 to 50% of the radius from Step F, more particularly the preset distance is between about 0.5 to 2 mm, and yet more particularly the preset distance is about 1 mm.
H. Find the equation of a parabola that best fits (by sum of squares analysis) the velocity data in that segment. In particular embodiments, the velocity data in that segment is the velocity data as a function of radius for each of N sections of the phase image. Thus, the equation of the parabola is fitted to all the velocity data of the N sections and not just one section at a time. N is an integer $\geq 2$ and in more particular embodiments is an integer in the range of from about 4 to 128 and yet in more particular embodiments N is 12.
I. Using the equation of the best-fit parabola, calculate the slope at where the velocity would equal zero. This is the shear rate of the artery. The radius at which the velocity would equal zero is the radius of the artery.

Thereafter, the flow is determined, Step 254. In a particular illustrative embodiment the flow is determined by summing the velocity pixels whose distance from the center is less than the radius where the velocity drops below the preset value or percentage of maximum. This is the flow in the artery.

In the case, where the center of the arterial cross-section was determined using the phase image (Step 246, phase), the radius of the arterial cross-section is determined, Step 256. In an exemplary illustrative embodiment the radius is calculated using the equation of the parabola fitted to the velocity data in Step H. As indicated herein the velocity is zero at the lumen-wall interface.

Alternatively, shear rate and/or radius can be determined using the following methodology in which image data also is imported into the microprocessor or computer for processing, such as for example imported into a spreadsheet-based program. The cardiac phase closest to peak systole was identified by choosing the image with the greatest peak velocity and was used for further analysis. In our approach, the limits of the arterial diameter were estimated in two orthogonal axes. An initial estimate of the center of the cross-section was calculated from those limits.

The cross-section was divided into 12 sectors around the estimated center. For each sector, outer radius of the velocity profile was estimated. A ring segment of datapoints with radius ranging from slightly less than the initially estimated outer radius to about 1 mm inward toward the estimated center was used. The velocity pixels in the ring segment of the sector were fit by least-squares method to a parabola with the assumption that blood flow velocity at the lumen wall is zero. Shear rate was calculated or measured as the slope of the velocity profile at the lumen-wall interface. Radius was calculated as the distance from the center of the velocity parabola to the point where the parabola crosses zero velocity.

The calculated lumen radius and shear values were averaged over the 12 sectors in the arterial cross-section. This approach provides sub-pixel precision in calculating lumen radius, and was shown to be accurate when compared to glass tubes of known manufactured diameter. Furthermore, the approach is not constrained by the geometry of the lumen perimeter, i.e. the arterial cross-section does not have to be perfectly circular. Systolic flow was measured directly by summing all of the velocity pixels in the arterial cross-section. Shear rate immediately after cuff inflation was calculated using flow measured at two minutes into cuff inflation, and using radius measured at baseline, using the Poiseuille equation:

$$\text{shear rate} = 4\, k(\text{flow})/((\pi)(\text{radius}^3))$$

The constant k is necessary because the velocity profile during systole is slightly blunted rather than being a fully developed parabola. Consequently the true shear rate is greater than what would be calculated using a fully developed parabolic velocity profile. Thus, k describes how many times greater the shear rate is than would be predicted by a fully developed paraboloid given the same radius and flow. The value of k was determined for each subject by directly measuring radius, flow, and shear rate at baseline and at 2-minutes into cuff inflation. The value of the k was solved for:

$$k=(\pi(\text{radius}^3))/(4(\text{flow})(\text{shear rate}))$$

The value of k at 2 minutes into cuff inflation was used in the calculation of shear rate immediately after cuff inflation. Degree of vasoconstriction was expressed as the percent change in radius from baseline to two minutes into cuff inflation. Degree of vasodilation was expressed as the percent change in radius from baseline to one minute after cuff release. Peak hyperemic shear rate is calculated from the images acquired immediately after cuff release.

After proceeding with Steps 240 and 242, the methodology returns to continue with Step 208 of FIG. 2A. Thereafter, the process described above for Steps 244-256 is conducted while image data for another vascular function is being acquired or the clinician or technician awaits the acquisition of all image data for all vascular functions to be evaluated and then conducts the process in these steps.

If vascular reactivity is not be evaluated (No, Step 206) or upon return of the process to Step 208 from, Step 242 of FIG. 2C, then the process continues with a determination if local arterial stiffness should be assessed, Step 206. If local arterial stiffness is to be assessed (Yes, Step 206) the process proceeds to Step 260 of FIG. 2D.

Figure 2D:
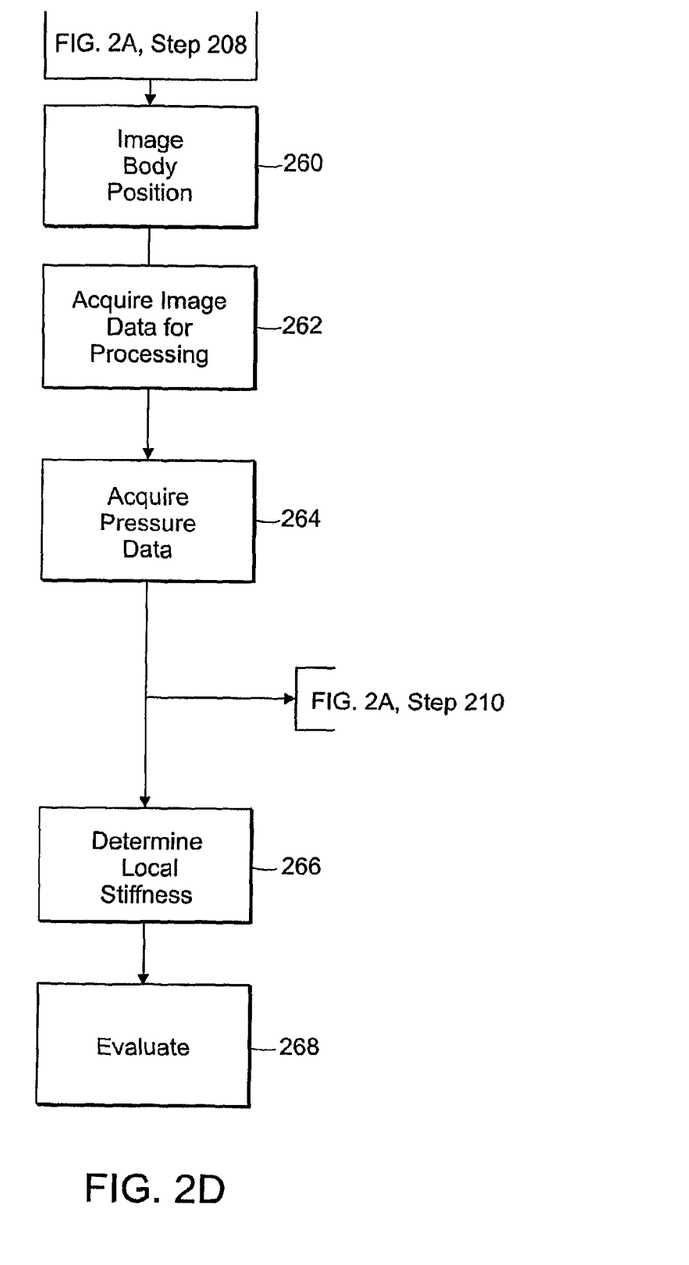

As indicated above, a blood pressure cuff, is disposed proximal the region being imaged so the cuff selectively occludes the artery and releases the pressure occluding the artery so that image data using MRI is acquired during the above described process, Step 260. At the same time the pressure data of the blood pressure cuff is acquired, Step 264. After the image data is obtained, the imaged data is acquired (i.e., imported into the computer) for processing, Step 262.

Using any of a number of techniques known to those skilled in the art, the acquired image data and pressure information is used to determine the local arterial stiffness, Step 266. For example, as is known to those skilled in the art, compliance of a blood vessel is related to changes in cross-sectional area and related changes in blood pressure (e.g., compliance=change in cross-sectional area/change in pressure, where the change in cross-sectional area=Systolic cross-sectional area–diastolic cross-sectional area and change in pressure=systolic pressure–diastolic pressure). Also, an evaluation is made using the determined local stiffness to determines if the determined stiffness value is indicative of age related stiffness or associated with an abnormal vascular condition or the potential for an abnormal vascular condition, Step 268.

After proceeding with Steps 260-264, the methodology returns to continue with Step 210 of FIG. 2A. Thereafter, the process described above for Steps 266-268 is conducted while image data for another vascular function is being acquired or the clinician or technician awaits the acquisition of all image data for all vascular functions to be evaluated and then conducts the process in these steps.

If local arterial stiffness is not be evaluated (No, Step 208) or upon return of the process to Step 210 from, Step 264 of FIG. 2D, the process determines if the data acquisition process is complete, Step 210. If the data acquisition process is not complete (No, Step 210), then the process returns to Step 202 and the process described above for steps 202-210 is repeated. If the data acquisition process is complete (Yes, Step 210) the data acquisition process is ended, Step 212. As indicated above, while the acquisition of data may be completed it is within the scope of the present invention for the data analysis and evaluation process described on FIGS. 2B-2D be continued thereafter.

Figure 4:
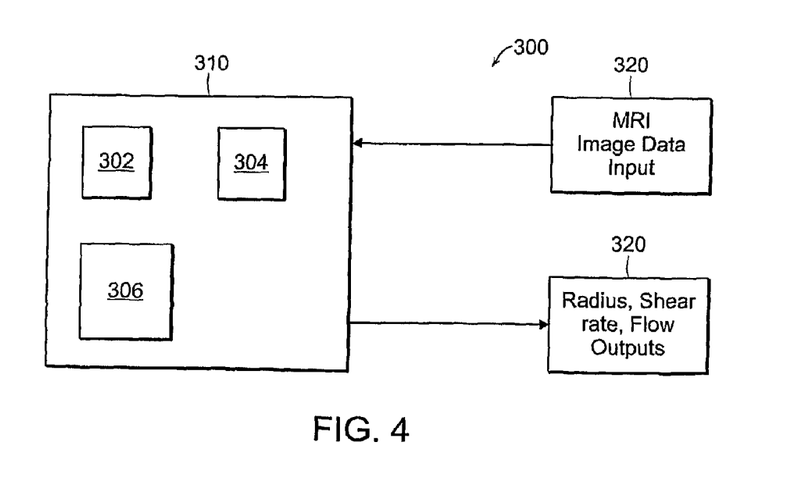
FIG. 4 is a schematic view of a computer system including an applications program embodying a methodology according to either aspect of the present invention for processing MRI image data

Referring now to FIG. 4 there is shown a schematic view of a computer system 300 for processing the image data and on which an applications program embodying any of the methodologies described herein is executed. Such a computer system 300 includes a computer 310 having a microprocessor 312, a memory 314 (e.g., RAM, NVRAM), and a storage device 316 on which programs such as the applications program embodying the methodology of the present invention and other information can be stored. The computer 310 receives MRI inputs 320 from MRI scanning or detection devices (e.g., coils). Such an applications program includes code segments, instructions and criteria for carrying out the methodology herein described. The computer 310 processes the MRI image data as herein described and provides outputs 330 of various parameters or characteristics of vascular function such as, but not limited to pulse flow velocity, shear rate, radius and flow.

EXAMPLE 1

Introduction:

Central arterial stiffness is a powerful predictor of atherosclerosis and cardiovascular events, and is associated with cardiovascular risk factors. One of the most important ways of measuring arterial stiffness is by measuring pulse wave velocity—pulse waves travel faster in stiffer vessels. Most MRI applications of pulse wave velocity to assess central arterial stiffness consist of measuring the difference in pulse wave arrival time between two sites in the aorta. However, the pulse wave arrives at the femoral artery just after traversing the central arteries, and the femoral artery is easily accessible by MRI.

Purpose:

To compare pulse wave arrival time at the femoral artery between two groups—one group with and the other group without cardiovascular risk factors.

Methods:

We studied 12 men—6 men 40 years of age or younger, with no cardiovascular risk factors; and 6 men over 50 years of age with type 2 diabetes. A four-element phased-array receiver coil was placed above and below the thigh, and later a 3-inch coil was placed at the medial surface of the right upper arm. An ECG-gated, phase-contrast MR pulse sequence was used with the following parameters: Matrix size 256×128, field-of-view 10 by 10 cm for the femoral artery and 8 by 8 cm for the brachial artery, 16 signal averages (NEX), slice thickness 3 mm, flip angle 25 degrees, bandwidth 31.2 kHz, repetition time (TR) 11.43 msec, echo time (TE) 5.25 msec, 8 views per segment, first order flow compensation, no phase-wrap, and no magnitude weighting. View-sharing was used to obtain 20 images per cardiac cycle. A user-independent algorithm was used to calculate instantaneous flow in the cross-section. Arrival time in an artery was calculated as the elapsed time after the R-wave trigger that it took for the instantaneous flow in the cross-section to reach 50% of its peak systolic value. The arrival time was normalized to path length by dividing by a normalized height ratio: the subject's height divided by 72 inches. The one-location method of assessing stiffness at the femoral artery was compared with a two-location method commonly used with applanation tonometry—the difference between arrival times in the brachial and femoral arteries was also calculated for each subject. The difference was then normalized to path length by dividing by the normalized height ratio.

Results:

Heart rate and height were not different between the two groups. Pulse wave arrival time was shorter in the older diabetic men compared with the young healthy men, whether measured in the femoral artery alone (88±15 vs. 146±33 msec, p=0.003), or by the difference in arrival times between the femoral and brachial arteries (36±21 vs. 89±37 msec, p=0.008). Pulse arrival time assessed at the brachial artery alone did not differ between older diabetic men and young healthy men (52±18 vs. 56±10 msec, p=0.37). See FIG. 3.

Conclusions:

Pulse wave arrival time at the femoral artery was shorter in older diabetic men than young healthy men, indicating stiffer central arteries. Using a single femoral site provided the same information as the more commonly used tonometric technique measuring the difference in arrival times between the femoral and brachial arteries. However, using a single accessible artery significantly simplifies the technique. Femoral artery MRI may be a novel and useful technique to measure central arterial stiffness.

Although a preferred embodiment of the invention has been described using specific terms, such description is for illustrative purposes only, and it is to be understood that chinges and variations may be made without departing from the spirit or scope of the following claims.

Incorporation by Reference

All patents, published patent applications and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Such equivalents are intended to be encompassed by the following

What is claimed is:

1. A method for assessing central arterial stiffness, comprising the steps of:
    locating an MRI detector proximal a single peripheral arterial location , the MRI detector being external to the body;
    acquiring image data of an arterial cross section of the single peripheral arterial location in a time sequence using an MRI process;
    determining from acquired image data an arrival or passage of one or more pulse waves in the single peripheral arterial location being imaged; and
    determining a central arterial stiffness related parameter using determined one or more pulse waves at the single peripheral arterial location and not using image data of another arterial location.

2. The method of claim 1, wherein said determining a central arterial stiffness related parameter includes:
    (a) associating timing of a cardiac function with timing of timing of each of the one or more pulse waves; and
    (b) determining a differential time between the timing of the cardiac function and the timing for each of the one or more pulse waves.

3. The method of claim 2, wherein said determining a central arterial stiffness related parameter further includes:
    determining a distance between a location of the MRI detector and a predetermined anatomical feature of a body being imaged; and
    calculating a pulse wave velocity using the differential time for each of the one or more pulse waves and a determined distance.

4. The method of claim 2, wherein said determining a central arterial stiffness related parameter further includes:
    determining an average differential time based on determined differential times for each of the one or more pulse waves;
    determining a distance between a location of the MRI detector and a predetermined anatomical feature of a body being imaged; and
    calculating a pulse wave velocity using the average differential time and a determined distance.

5. The method of claim 2, wherein the cardiac function is a R-wave trigger.

6. The method of claim 1, wherein the single peripheral arterial location is selected so that the one or more pulse wave traverse central arteries before arriving at the location being imaged.

7. The method of claim 1, wherein the single peripheral arterial location is the femoral artery.

8. The method of claim 1, wherein said determining a central arterial stiffness related parameter includes:
    determining a pulse wave arrival time for each of the one or more pulse waves, wherein the arrival time is an elapsed time after occurrence of a specific cardiac function and a time of a corresponding pulse wave as determined from the acquired imaged data;
    determining the central arterial stiffness related parameter using each determined pulse wave arrival time for each of the one or more pulses waves.

9. The method of claim 8, wherein said determining a central arterial stiffness related parameter further includes:
    determining a distance between a location of the MRI detector and a predetermined anatomical feature of a body being imaged; and
    calculating a pulse wave velocity using the pulse wave arrival times and a determined distance.

10. The method of claim 8, wherein said determining a central arterial stiffness related parameter further includes:
    determining an average pulse wave arrival time based on the determined pulse wave arrival times for each of the one or more pulse waves;
    determining a distance between the location of the MRI detector and a predetermined anatomical feature of the body being imaged; and
    calculating a pulse wave velocity using the average pulse wave arrival time and a determined distance.

11. A method for assessing vascular function comprising the steps of:
    assessing central arterial stiffness;
    assessing vascular reactivity; and
    wherein said assessing central arterial stiffness includes:
    locating an MRI detector proximal a single peripheral arterial location, the MRI detector being external to a body,
    acquiring image data of an arterial cross section of the single peripheral arterial location in a time sequence using an MRI process,
    determining from the acquired image data an arrival or passage of one or more pulse waves in the single peripheral arterial location being imaged, and
    determining a central arterial stiffness related parameter using determined one or more pulse waves at the single peripheral arterial location and not using image data of another arterial location.

12. The method of claim 11, wherein said assessing vascular reactivity includes:

using a magnetic resonance imaging scanner to obtain images, locating an artery using coronal scout images, positioning a subject or patient, such that the artery is parallel to a magnet bore of the magnetic resonance imaging scanner and cross sectional images can be thus obtained, constricting the artery for a time period, whereby the artery is fully occluded, acquiring images of the artery prior to occlusion (at baseline), as well as one or more times during occlusion and as well as after occlusion release, and using the acquired image data and measuring a shear rate and/or radius of the artery at baseline, for each of the one or more times during occlusion and after occlusion release.

13. The method of claim 11, wherein said determining a central arterial stiffness related parameter includes:

associating timing of a cardiac function with timing of each of the one or more pulse waves, and determining a differential time between the timing of the cardiac function and the timing for each of the one or more pulse waves.

14. The method of claim 13, wherein said determining a central arterial stiffness related parameter further includes:

determining a distance between a location of the MRI detector and a predetermined anatomical feature of the body being imaged, and calculating a pulse wave velocity using the differential time for each of the one or more pulse waves and the determined distance.

15. The method of claim 13, wherein said determining a central arterial stiffness related parameter further includes:

determining an average differential time based on determined differential times for each of the one or more pulse waves, determining a distance between the location of the MRI detector and a predetermined anatomical feature of the body being imaged, and calculating a pulse wave velocity using the average differential time and a determined distance.

16. The method of claim 11, wherein the single peripheral arterial location is selected so that the pulse wave traverse central arteries before arriving at the location being imaged.

17. The method of claim 11, wherein the single peripheral arterial location is the femoral artery.

* * * * *